United States Patent [19]

Auditore-Hargreaves et al.

[11] 4,446,233

[45] May 1, 1984

[54] HOMOGENEOUS IMMUNOASSAY USING COVALENT HYBRID ANTIBODIES

[75] Inventors: Karen Auditore-Hargreaves; Frederick M. Miesowicz, both of Wilmington, Del.

[73] Assignee: E. I. Du Pont de Nemours and Company, Wilmington, Del.

[21] Appl. No.: 374,970

[22] Filed: May 5, 1982

[51] Int. Cl.³ .................... G01N 33/54; G01N 33/58
[52] U.S. Cl. ........................... 435/7; 436/537; 436/547; 436/817
[58] Field of Search ............... 436/537, 547, 817; 435/7

[56] References Cited

U.S. PATENT DOCUMENTS 3,817,837  6/1974  Rubenstein et al. .
3,935,074  1/1976  Rubenstein et al. .

FOREIGN PATENT DOCUMENTS 34050  8/1981  European Pat. Off. .

OTHER PUBLICATIONS

Chemical Abstracts, 86:119045j and 119046k, (1977).
V. Raso et al., Cancer Research, 41, 2073–2078, (Jun. 1981).
A. Nisonoff et al., Archives of Biochemistry and Biophysics, 93(1), 460–462, (Apr. 1961).
Hammerling et al., J. Exp. Med., 128, 1461, (1968).
Hong et al., J. Biol. Chem., 240, 3883, (1965).

*Primary Examiner*—Sidney Marantz

[57] ABSTRACT

An immunoassay for analytes such as antigens or haptens, which utilizes covalent hybrid antibodies to modulate the activity of indicators. The hybrid antibody has binding sites for the analyte and the indicator. Final activity of the indicator is proportional to analyte concentration.

4 Claims, No Drawings

HOMOGENEOUS IMMUNOASSAY USING COVALENT HYBRID ANTIBODIES

DESCRIPTION

1. Technical Field

This invention relates to homogeneous immunoassay methods for the measurement of large molecular weight antigens and haptens in biological fluids and more particularly to such immunoassays using covalent hybrid antibodies to modulate the activity of enzyme indicators, to bring two enzymes into close spatial proximity, or to modulate the aggregation of latex particles.

2. Background Art

Competitive binding immunoassays are widely used to determine qualitatively or quantitatively the presence of a ligand in a liquid medium. One type of such assays, referred to as homogeneous immunoassays, utilizes a specific ligand receptor which interacts with a ligand-indicator conjugate to modify the indicator in a measureable way. The indicator is usually an enzyme.

U.S. Pat. No. 3,817,837, issued June 18, 1974 to Rubenstein, et al., discloses a homogeneous competitive binding immunoassay in which the activity of the indicator label in a label-ligand conjugate is modulated by the binding of the antibody to the ligand.

U.S. Pat. No. 3,935,074, issued Jan. 27, 1976 to Rubenstein, et al., discloses a method of utilizing a reagent having two epitopes, one common to the ligand of interest and one foreign to the ligand (the indicator label). Simultaneous binding of two antibodies to the epitopes is sterically inhibited. Measurement of the bound or unbound antibody to the indicator label epitope is used to provide a measure of the quantity of ligand in the unknown sample.

Hammerling, et al., J.Exp.Med., Volume 128, 1461 (1968), disclose the electron microscopic visualization of cell surfaces using antibodies consisting of two Fab' fragments linked by a disulfide bond. One Fab' is specific for a cell surface antigen and the other is specific for a marker which is visible by electron microscopy. This assay technique is not generally adaptable to soluble antigens and requires sophisticated instrumentation.

European patent application No. 034,050, published Aug. 19, 1981 discloses a homogeneous immunoassay for antigens and haptens utilizing a mixed binding reagent containing an antigen-binding site and a label-binding site, the two sites being spaced apart so that a single molecule of an antigen-label conjugate cannot bind to both sites. The label is one whose activity is changed upon binding to the label-binding site of the mixed binding reagent. Measurement of the activity of the label is indicative of the amount of antigen in a liquid sample. The mixed binding reagent consists of two different intact immunoglobulin molecules being linked together to form a unitary reagent complex.

Hybrid antibodies are heterobifunctional antibodies having two different and spatially distinct binding sites, each for a different antigen and have been described, for example, by Hong, et al., J. Biol. Chem., Volume 240, 3883 (1965).

There are discernible advantages in using covalent hybrid antibodies in homogeneous immunoassays for soluble antigens.

DISCLOSURE OF THE INVENTION

The homogeneous immunoassay of this invention for the measurement of various analytes comprises the steps of incubating sequentially or simultaneously:

(A) a substantially pure covalent hybrid antibody consisting essentially of two different heavy chain-light chain half-molecules, wherein the first of said half-molecules provides a binding site for a first antigen and the second of said half-molecules provides a chemically different binding site for the first or a second antigen; wherein said half-molecules are bonded to each other through disulfide linkage;

(B) biological sample containing analyte;

(C) an indicator; and (D) reagents for signal-generating reaction.

DESCRIPTION OF THE INVENTION

The homogeneous immunoassay methods of this invention for the measurement of various analytes such as large molecular weight antigens and haptens in biological fluids utilize covalent hybrid antibodies to modulate the activity of an enzyme indicator, to bring two enzymes into close spatial proximity or to modulate the aggregation of latex particles.

Covalent hybrid antibodies are heterobifunctional antibodies having two different and spatially distinct binding sites, joined through inter-heavy chain disulfide bond(s), each capable of recognizing a different antigen or the same antigen but at differing locations on the antigen. These covalent hybrid antibodies and their preparation are described in copending patent application, Ser. No. 374,971, filed May 5, 1982, hereby incorporated by reference.

The covalent hybrid antibodies utilized in this invention are preferentially produced by an ordered covalent hybridization of the inter-heavy chain disulfide bonds of intact immunoglobulin molecules of the IgG class as is described in the copending application referred to above. The covalent hybrid antibody contains one binding site specific for an analyte of interest present in the biological sample and one binding site specific for an indicator.

The ordered hybridization of IgG molecules to provide hybrid antibodies having different antigen-binding specificites can be accomplished by different procedures. In one procedure, S-sulfonated half-molecules are derived from a first IgG by sulfitolysis as described above. The protein product (immunoglobulin half-molecules) can be separated from the other products of the sulfitolysis reaction by dialysis against a suitably buffered medium through which nitrogen is bubbled at room temperature. Sulfhydryl-containing half-molecules are derived from a second IgG by one of the methods described above.

Removal of the thiol reagent, where one is present, can be accomplished without reoxidation of the protein either by gel filtration or by dialysis in a buffered medium of pH 5, containing, for example, ethylene diamine tetraacetic acid, which has been thoroughly degassed and through which nitrogen is bubbled. The two different populations of half-molecules generated by these methods are then combined in equimolar amounts and dialyzed under anaerobic conditions in a suitably buffered medium (containing strontium chloride or another alkali earth metal salt). A nucleophilic displacement reaction, shown below, affords the desired hybrid antibody product in which the dissimilar halves are joined together by disulfide linkage.

$$R-S-SO_3^- + R'-SH \rightarrow R-S-S-R' + HSO_3^-$$

where
R is $H_1^a L_1^a$ and
R' is $H_1^b L_1^b$

In another procedure of hybridization, S-sulfonated half-molecules are derived from a first IgG by sulfitolysis, as described above. Sulfhydryl-containing half-molecules are derived from a second IgG as described above in the third method for selective cleavage of the inter-H chain bonds. The bound IgG half-molecules, however, are not eluted from the support (such as antigen coated beads or Protein A immobilized on Sepharose gel) to which they are bound. Instead, the support is washed by suspending in a suitable buffer, followed by centrifugation, to remove the thiol reagent. The S-sulfonated half-molecules of the first IgG are then added to the bound sulfhydryl containing half-molecules of the second IgG in a suitably buffered medium, containing strontium chloride, and incubated at room temperature in an inert atmosphere. The hybrid antibodies so produced, formed on the support surface by nucleophilic displacement, can be eluted with a buffer containing an appropriate chaotropic agent (for example, high-salt concentration solution or surfactant).

By analyte of interest in the biological sample is meant the substance whose concentration is desired to be determined. The biological sample can be biological fluids such as whole blood, blood serum, blood plasma, saliva, cerebral spinal fluid or urine or can be cell and tissue extracts. The analyte is often a protein present in one of these biological fluids but also includes drugs, hormones, vitamins, enzymes, antibodies, polysaccharides, bacteria, protozoa, fungi, viruses, cell and tissue antigens and other blood cell or blood fluid substances.

In the first aspect of the invention, the indicator is an enzyme whose activity can be modulated upon binding to the hybrid antibody. A specific β-galactosidase is one preferred enzyme for use in the immunoassay of this invention. This enzyme is isolated from strain #W6101 lac z⁻ of *E. coli* known as the AMEF (antibody modulated enzyme fragment) mutant. Antibodies to wild-type β-galactosidase can specifically activate this mutant enzyme. This modulation can also occur with univalent antibody fragments (Fab) and, therefore, by binding to one binding site on the hybrid antibody. Other potential indicator enzymes whose activities are modulated upon antibody binding include phenylalanine hydroxylase, penicillinase, glucose oxidase and human prostatic acid phosphatase. Other nonenzyme indicators can also be functional in the immunoassay method of this invention including fluorophores, radioactive materials, and bio- or chemiluminescent materials. While modulation will usually take the form of activation of indicator activity, inactivation is also possible.

The binding of analyte to the analyte-specific binding site inhibits the binding of the indicator to the indicator-specific binding site of the hybrid antibody. Thus, since the indicator activity is not modulated when the analyte binding site is filled, the measured activity of the indicator at the completion of the assay is proportional to the concentration of analyte in the biological fluid.

The immunoassay of this invention provides good sensitivity when compared to competitive-binding homogeneous immunoassays since the binding of one analyte molecule to the hybrid antibody substantially completely modulates the activity of the indicator, that is, it is a direct immunoassay. In conventional assays, more than one analyte molecule can be bound to the bivalent antibody and the modulation of the activity of the indicator or label may not be substantially complete upon the binding of a single analyte molecule to the antibody.

In certain circumstances, the analyte of interest is not sufficiently large to hinder the binding of the enzyme indicator to the covalent hybrid antibody. In these cases, an analyte conjugate (in known concentration) can be used in the method of this invention. The analyte conjugate and free analyte compete for binding to the hybrid antibody. The binding of the analyte conjugate sterically or ionically inhibits the binding of the enzyme indicator, thus preventing the modulation of activity. Such analyte conjugates, for example, can be analytes covalently bound to a high molecular weight carrier protein or to latex particles.

Optionally, the hybrid antibody can be modified, for example, by glutaraldehyde crosslinking to reduce the segmental flexibility in the hinge region, and thereby eliminating the need for a large analyte to sterically hinder the binding of the enzyme indicator.

The homogeneous hybrid antibody immunoassay of this invention can be performed by mixing and incubating the hybrid antibody, the enzyme indicator, and a biological fluid containing an unknown quantity of analyte. Reagents for the detection of the enzyme indicator can then be added to measure the modulated activity of the enzyme indicator. Optionally, an analyte conjugate can be utilized in the first mixing and incubation step for the measurement of analytes of low molecular weight. Also, optionally, the hybrid antibody can be pre-incubated with the biological fluid prior to adding the enzyme indicator.

The reagents for the detection of the enzyme indicator are dependent upon the enzyme indicator being utilized. These reagents can be chromogenic or fluorogenic substrates specific for the enzyme indicator. Other means of measuring enzyme activity such as electrochemically can also be employed in the method of this invention.

The measurement of color produced by the enzymatic cleavage of a chromogenic substrate is proportional to the modulated enzyme indicator activity. This activity, in turn, is a function of the amount of analyte in the biological fluid. Therefore, by performing the immunoassay on a series of samples containing known analyte concentrations, the unknown concentration of analyte in a biological fluid can be determined.

In a second aspect, the method of this invention also utilizes covalent hybrid antibody with one binding site specific for analyte and the other site specific for enzyme indicator. In this case, however, the activity of the enzyme indicator need not be modulated upon binding to the hybrid antibody. The hybrid antibody functions to bring the enzyme indicator and an enzyme-analyte conjugate in close spatial proximity. The enzyme indicator and a different second enzyme in the enzyme-analyte conjugate are chosen such that the product of one enzyme-catalyzed reaction is a substrate for the other enzyme. This way, when both enzymes are bound to the hybrid antibody in close spatial proximity (150 Å), an enhancement of the rate of final product formation is observed. It should be noted that one of the two enzymes is not bound to the hybrid antibody directly but through the analyte with which it is conjugated. Free analyte from the biological fluid competes with the binding of the enzyme-analyte conjugate. Therefore, the higher the level of analyte, the less of the enzyme-analyte conjugate will be bound to the hybrid antibody leading to a lower rate enhancement. An inverse relationship is thus observed between the enzyme reaction rate and the concentration of analyte in the biological fluid.

A preferred enzyme system for use in this aspect of the invention is horseradish peroxidase as the indicator enzyme and glucose oxidase as part of the enzyme-analyte conjugate. Glucose oxidase catalyzes the production of hydrogen peroxide in the presence of glucose and water. The hydrogen peroxide thus formed is a substrate for horseradish peroxidase which, in the presence of a suitable chromogenic substrate, will catalyze color formation at a rate proportional to hydrogen peroxide concentration. As discussed above, the rate of color formation is inversely related to the analyte concentration in the biological fluid.

In a third aspect, the method of this invention utilizes covalent hybrid antibody with one binding site specific for analyte and the other site specific for an aggregating substance, the indicator. By aggregating substance is meant a multivalent protein, a polyhapten-protein conjugate or hapten, each of which is attached to a latex particle. An example of latex particles useful in the method of this invention is described in U.S. patent application Ser. No. 315,922, filed Oct. 28, 1981.

The method of the third aspect of the invention can be carried out in two steps. The first step is a binding step in which the hybrid antibody, analyte from the the biological fluid, and a polyanalyte (a signal generating reagent) such as a polyvalent analyte-protein conjugate, are mixed. The hybrid antibody can bind to either the free analyte from the biological fluid or to the polyanalyte with one of its binding sites. In the second step, the aggregating substance is added and the hybrid antibody-polyanalyte complexes combine with the aggregating substance to cause aggregation. This results in an increase in turbidity which can be measured spectrophotometrically. The level of aggregation is inversely proportional to the concentration of analyte in the biological fluid.

EXAMPLE

Enzyme Activation Immunoassay Employing a Hybrid Antibody Reagent

An immunoassay for a large molecular weight analyte will utilize the following materials:
(a) covalent hybrid antibody reagent as described in Example 1 of Ser. No. 374,971, having binding specificities for the analyte and an enzyme indicator;
(b) signal-producing enzyme indicator reagent, whose activity is modulated by binding to the covalent hybrid antibody;
(c) reagents for the colorimetric or fluorimetric signal-generating reaction; and
(d) biological sample containing analyte which is a protein of molecular weight $\geq 10,000$ but more often $\geq 100,000$.

The biological sample can be a serum sample, a urine sample or a whole blood sample. The enzyme indicator can be an enzyme or enzyme subunit which is inactive unless bound by antibody; for example, the AMEF mutant of $E.$ $coli$ $\beta$-galactosidase or human prostatic acid phosphatase. The enzyme indicator can also be an active enzyme which is inactivated by the binding of antibody. The reagents for the signal-generating reaction are chromogenic or fluorogenic substrates of the enzyme indicator plus any additional necessary cofactors or cations in an aqueous buffer of pH 4–10.

It is expected that materials (a), (b), and (d) will be incubated together for a time at a temperature between 0° and 50° C., more often between 22° and 46° C., before adding the reagents (c). However, in certain instances, it may be desirable to preincubate component (a) and (d) before the addition of the enzyme indicator. Likewise, it is possible that all materials are added simultaneously. The length of incubation will usually be less than 30 minutes, more often 1–4 minutes. Measurement of the signal produced by the enzyme will usually be made in less than 30 minutes after addition of material (c) and more often in less than 3 minutes.

Where the enzyme indicator is inactive and becomes active only when bound by antibody, the amount of signal produced will be inversely proportional to the concentration of analyte in the sample. Where the enzyme-indicator is active and is inactivated when bound by antibody, the amount of signal produced will be directly proportional to the concentration of analyte in the sample.

We claim:
1. A homogeneous immunoassay for the measurement of analyte comprising the steps of incubating sequentially or simultaneously:
(A) a substantially pure covalent hybrid antibody consisting essentially of two different heavy chain-light chain half-molecules, wherein the first of said half-molecules provides a binding site for a first antigen and the second of said half-molecules provides a chemically different binding site for the first or a second antigen; wherein said half-molecules are bonded to each other through disulfide linkage;
(B) a biological sample containing analyte;
(C) an indicator capable of being bound by said hybrid antibody; and
(D) reagents for signal-generating reaction.

2. The homogeneous immunoassay of claim 1 wherein the indicator is an enzyme and the reagents for signal-generating reaction include enzyme substrates.

3. The homogeneous immunoassay of claim 1 wherein the indicator is an aggregating substance and the reagents for signal-generating reaction include polyanalytes.

4. The homogeneous immunoassay as in one of claims 1–3 wherein the analyte is selected from the group consisting of protein, hormone, drug, vitamin, enzyme, antibody, polysaccharide, bacteria, protozoa, fungi, virus, cell and tissue antigens.

* * * * *